US012788993B2

(12) United States Patent
Ippolito et al.

(10) Patent No.: US 12,788,993 B2
(45) Date of Patent: Nov. 10, 2026

(54) ACTIVITY DETECTION FOR CARDIAC REMODELING PACING

(71) Applicant: Medtronic, Inc., Minneapolis, MN (US)

(72) Inventors: Ekaterina M. Ippolito, Shoreview, MN (US); Troy E. Jackson, Rogers, MN (US); Abhijit Kadrolkar, St. Paul, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 877 days.

(21) Appl. No.: 18/101,804

(22) Filed: Jan. 26, 2023

(65) Prior Publication Data

US 2023/0241401 A1 Aug. 3, 2023

Related U.S. Application Data

(60) Provisional application No. 63/304,166, filed on Jan. 28, 2022.

(51) Int. Cl.
*A61N 1/365* (2006.01)

(52) U.S. Cl.
CPC ................................ *A61N 1/36542* (2013.01)

(58) Field of Classification Search
None
See application file for complete search history.

(56) References Cited

U.S. PATENT DOCUMENTS

| | | | |
|---|---|---|---|
| 4,428,378 | A | 1/1984 | Anderson et al. |
| 4,567,892 | A | 2/1986 | Plicchi et al. |
| 4,644,954 | A | 2/1987 | Wittkampf et al. |
| 4,867,161 | A | 9/1989 | Schaldach |
| 4,884,576 | A | 12/1989 | Alt |
| 5,052,388 | A | 10/1991 | Sivula et al. |
| 5,052,454 | A | 10/1991 | Meinhardt |
| 5,097,831 | A | 3/1992 | Lekholm |
| 5,197,467 | A | 3/1993 | Steinhaus et al. |
| 5,292,340 | A | 3/1994 | Crosby et al. |
| 5,318,597 | A | 6/1994 | Hauck et al. |
| 5,630,834 | A | 5/1997 | Bardy |
| 5,876,353 | A | 3/1999 | Riff |
| 6,298,268 | B1 | 10/2001 | Ben-Haim et al. |

(Continued)

FOREIGN PATENT DOCUMENTS

| | | |
|---|---|---|
| EP | 2809393 | 12/2014 |
| WO | 2005/039690 | 5/2005 |

(Continued)

OTHER PUBLICATIONS

International Search Report and Written Opinion for PCT/US2023/011689 dated Apr. 21, 2023 (13 pages).

(Continued)

*Primary Examiner* — Shirley X Jian
(74) *Attorney, Agent, or Firm* — Mueting Raasch Group

(57) ABSTRACT

Patient activity or inactivity may be determined based, at least in part, on a movement signal representative, or indicative, of movement of a patient. When the patient is determined to be inactive based the movement signal monitored over a moving time window, cardiac remodeling pacing may be delivered to the patient.

24 Claims, 8 Drawing Sheets

(56) References Cited

U.S. PATENT DOCUMENTS

| | | | |
|---|---|---|---|
| 6,314,322 | B1 | 11/2001 | Rosenberg |
| 6,650,937 | B2 | 11/2003 | Kerver |
| 7,133,718 | B2 | 11/2006 | Bakken et al. |
| 7,194,306 | B1 | 3/2007 | Turcott |
| 7,305,266 | B1 | 12/2007 | Kroll |
| 7,445,605 | B2 | 11/2008 | Overall et al. |
| 7,630,078 | B1 | 12/2009 | Nabutovsky et al. |
| 7,660,616 | B1 | 2/2010 | Poore |
| 7,769,451 | B2 | 8/2010 | Yang et al. |
| 7,840,246 | B1 | 11/2010 | Poore |
| 7,941,216 | B2 | 5/2011 | Salo et al. |
| 8,027,724 | B2 | 9/2011 | Wei et al. |
| 8,046,069 | B2 | 10/2011 | Kramer et al. |
| 8,065,003 | B2 | 11/2011 | Kenknight et al. |
| 8,126,549 | B2 | 2/2012 | Sigg et al. |
| 8,306,615 | B2 | 11/2012 | Brockway et al. |
| 8,386,038 | B2 | 2/2013 | Bianchi et al. |
| 8,600,497 | B1 | 12/2013 | Yang et al. |
| 8,606,356 | B2 * | 12/2013 | Lee ........................ A61B 5/113 607/17 |
| 8,798,751 | B2 | 8/2014 | Spear et al. |
| 8,805,497 | B2 | 8/2014 | Dong et al. |
| 8,838,215 | B2 * | 9/2014 | John ...................... A61B 5/349 607/18 |
| 8,996,101 | B2 | 3/2015 | Zhang et al. |
| 9,002,454 | B2 | 4/2015 | Ghosh et al. |
| 9,101,772 | B2 | 8/2015 | Kleckner et al. |
| 9,155,896 | B2 | 10/2015 | Salo |
| 9,320,906 | B2 | 4/2016 | Maskara et al. |
| 9,370,662 | B2 * | 6/2016 | Mika .................. A61N 1/36564 |
| 9,403,016 | B2 * | 8/2016 | Meyer ................ A61N 1/36535 |
| 9,956,416 | B2 | 5/2018 | Ghosh et al. |
| 10,029,103 | B2 | 7/2018 | Sweeney |
| 10,702,698 | B2 | 7/2020 | Zhao et al. |
| 11,207,529 | B2 | 12/2021 | Zhou |
| 11,311,734 | B2 | 4/2022 | Zhou |
| 11,318,314 | B2 * | 5/2022 | Sharma ................ A61B 5/0205 |
| 12,239,840 | B2 * | 3/2025 | Sharma .............. A61N 1/36592 |
| 12,508,428 | B2 * | 12/2025 | Hoffman .............. A61N 1/3627 |
| 2003/0158584 | A1 | 8/2003 | Cates et al. |
| 2004/0199210 | A1 | 10/2004 | Shelchuk |
| 2005/0076908 | A1 * | 4/2005 | Lee ........................ A61B 5/086 600/544 |
| 2006/0100668 | A1 | 5/2006 | Ben-David |
| 2006/0178586 | A1 | 8/2006 | Dobak, III |
| 2006/0224196 | A1 | 10/2006 | Hettrick et al. |
| 2006/0224203 | A1 | 10/2006 | Hettrick et al. |
| 2006/0247692 | A1 | 11/2006 | Yang et al. |
| 2007/0150017 | A1 | 6/2007 | Salo |
| 2007/0203522 | A1 | 8/2007 | Hettrick et al. |
| 2007/0208263 | A1 * | 9/2007 | John ...................... A61B 5/358 600/509 |
| 2008/0051840 | A1 | 2/2008 | Moaddeb et al. |
| 2008/0114408 | A1 | 5/2008 | Shuros et al. |
| 2008/0119898 | A1 | 5/2008 | Ben-David et al. |
| 2008/0132800 | A1 | 6/2008 | Hettrick et al. |
| 2008/0188721 | A1 | 8/2008 | Patangay et al. |
| 2008/0221636 | A1 * | 9/2008 | Pastore .............. A61N 1/36521 607/18 |
| 2008/0234776 | A1 | 9/2008 | Kenknight et al. |
| 2009/0005831 | A1 | 1/2009 | Wilson et al. |
| 2009/0093857 | A1 | 4/2009 | Markowitz et al. |
| 2009/0234401 | A1 | 9/2009 | Zielinski et al. |
| 2010/0016923 | A1 | 1/2010 | Rousso et al. |
| 2010/0082077 | A1 | 4/2010 | Bruns |
| 2010/0152802 | A1 | 6/2010 | Min |
| 2010/0152804 | A1 | 6/2010 | Kleckner et al. |
| 2012/0010674 | A1 | 1/2012 | Pastore et al. |
| 2012/0035679 | A1 | 2/2012 | Dagan et al. |
| 2012/0101541 | A1 | 4/2012 | Corbucci et al. |
| 2012/0150252 | A1 | 6/2012 | Feldman et al. |
| 2012/0303078 | A1 | 11/2012 | Li et al. |
| 2012/0323099 | A1 | 12/2012 | Mothilal et al. |
| 2013/0237873 | A1 | 9/2013 | Zhang et al. |
| 2014/0002772 | A1 | 1/2014 | Yang et al. |
| 2014/0100621 | A1 | 4/2014 | Feldman et al. |
| 2014/0277237 | A1 | 9/2014 | Maskara et al. |
| 2014/0303078 | A1 | 10/2014 | Melton et al. |
| 2015/0250428 | A1 | 9/2015 | Zhang et al. |
| 2016/0361559 | A1 | 12/2016 | Scharmer |
| 2017/0079598 | A1 | 3/2017 | Stolen et al. |
| 2017/0290550 | A1 | 10/2017 | Perschbacher et al. |
| 2018/0126171 | A1 | 5/2018 | Herrmann et al. |
| 2019/0167972 | A1 | 6/2019 | Stahmann et al. |
| 2019/0167991 | A1 | 6/2019 | Stahmann et al. |
| 2019/0168007 | A1 | 6/2019 | Stahmann et al. |
| 2019/0201696 | A1 | 7/2019 | Koop et al. |
| 2019/0336096 | A1 | 11/2019 | Itu et al. |
| 2019/0381322 | A1 * | 12/2019 | Sharma ................ A61N 1/3627 |
| 2019/0381323 | A1 * | 12/2019 | Sharma .............. A61N 1/36592 |
| 2020/0038663 | A1 | 2/2020 | Meyer |
| 2020/0289829 | A1 | 9/2020 | Ghosh |
| 2023/0241401 | A1 * | 8/2023 | Ippolito ............. A61N 1/36542 607/19 |

FOREIGN PATENT DOCUMENTS

| | | |
|---|---|---|
| WO | 2005/118062 | 12/2005 |
| WO | 2008/109040 | 9/2008 |
| WO | 2013/010165 | 1/2013 |
| WO | 2018/067931 | 4/2018 |

OTHER PUBLICATIONS

Boehmer et al., "A Multisensor Algorithm Predicts Heart Failure Events in Patients with Implanted Devices: Results from the MultiSENSE Study, JACC", Heart Failure, vol. 5, No. 3, 2017, pp. 216-225.

Gimelli et al., "CRT in Patients with Heart Failure: Time Course of Perfusion and Wall Motion Changes," 2010, Cardiology Research and Practice, 2010:981064, 5 pages.

Jarvelainen et al., "Extracellular Matrix Molecules: Potential Targets in Pharmacotherapy," Pharmacol Rev, 2009, 61:198-223.

Solomon et al., "Effect of Cardiac Resynchronization Therapy on Reverse Remodeling and Relation to Outcome", American Heart Association, vol. 122, , Sep. 7, 2010, pp. 985-992.

Westermann et al., "Role of left ventricular stiffness in heart failure with normal ejection fraction," Circulation, Apr. 22, 2008: 117 (16):2051-60.

International Search Report and Written Opinion for PCT/US2021/037229 dated Oct. 29, 2019 (21 pages).

Hirsch et al., "Respiratory Sinus Arrhythmia in Humans: How Breathing Pattern Modulates Heart Rate," Department of Physiology, State University of New York at Buffalo, School of Medicine, Buffalo, New York, pp. H620-H629.

Blain et al., "Influences of Breathing Patterns on Respiratory Sinus Arrhythmia in Humans During Exercise", Am J Physiol Heart Circ Physiol 288, H887-H895, 2005.

Shanks, J., et al. "Reverse re-modelling chronic heart failure by reinstating heart rate variability." Basic Research in Cardiology 117.1 (2022): 1-16.

Klein, F.J., et al., Heart-Rate Induced Modifications of Concentric Left Ventricular Hypertrophy—Exploration of a Novel Therapeutic Concept. Am J Physiology, Published Sep. 2, 2016 vol. No. , DOI: 10.1152/ajpheart.00301.2016.

Wahlberg K, Arnold ME, Lustgarten D, Meyer M. Effects of a Higher Heart Rate on Quality of Life and Functional Capacity in Patients With Left Ventricular Diastolic Dysfunction. Am J Cardiol. 2019; 124(7):1069-75.

Infeld, Margaret, et al. "Personalized pacing (myPace): a new paradigm for diastolic heart failure treatment." Journal of the American College of Cardiology 77.18_Supplement_1 (2021): 223-223.

Jian, A., et al. "Association Between Heart Rate Variability and Echocardiographic Parameters in Heart Failure with Reduced and Preserved Ejection Fraction." Heart, Lung and Circulation 28 (2019): S161.

(56) References Cited

OTHER PUBLICATIONS

Heidenreich, P.A., et al., Forecasting the impact of heart failure in the United States: a policy statement from the American Heart Association. Circ Heart Fail, 2013. 6(3): p. 606-19.
Owan, T.E., et al., Trends in prevalence and outcome of heart failure with preserved ejection fraction. N Engl J Med, 2006. 355(3): p. 251-9.

* cited by examiner

500

ACTIVITY DETECTION FOR CARDIAC REMODELING PACING

This application claims the benefit of U.S. Provisional Patent Application No. 63/304,166 entitled "Activity Detection for Cardiac Remodeling Pacing" and filed on Jan. 28, 2022, which is incorporated by reference in its entirety.

The present technology is generally related to activity detection for cardiac remodeling pacing, e.g., for treating heart failure (HF).

HF occurs when the heart muscle is unable to pump enough blood to meet the body's needs. The volume of blood pumped by the heart is determined by how well the heart squeezes (i.e., muscle contraction) and how well the heart relaxes and fills with blood. Ejection fraction is a measure of how much blood inside the left ventricle (LV) is pumped out with each contraction. When the left ventricle pumps, not all the blood in the ventricle leaves. A normal ejection fraction is more than about 50%. Heart failure with preserved ejection fraction (HFpEF) occurs when the left ventricle does not fill with blood as well as normal, but the ventricle can pump well. For example, the ventricle is stiff, or has thick walls, such that the ventricle doesn't relax to fill with a normal volume of blood. Alternatively, when the muscle contraction is abnormal (e.g., the muscle is too weak to pump properly), the condition is referred to as heart failure with reduced ejection fraction (HFrEF).

Patients with HFpEF represent nearly half of the heart failure population and continue to increase in prevalence relative to patients with HFrEF. Although patients with HFpEF experience outcomes as poor as those for patients with HFrEF, no evidence-based therapy to improve mortality and morbidity exists. The present technology is directed to algorithms for selecting a pacing therapy for a heart failure patient, such as one with HFpEF, based on monitored patient parameters that also account for interactions among various pacing therapies. The algorithms and pacing therapies may be implemented by implantable medical devices (IMDs) such as implantable cardioverter defibrillators (ICDs), cardiovascular implantable electronic devices (CIEDs), pacemakers, and cardiac resynchronization therapy (CRT) devices that, in some cases, include defibrillation capability (CRT-D devices).

SUMMARY

Embodiments described herein are directed to methods and devices for cardiac remodeling. One illustrative cardiac remodeling pacing method may include receiving a movement signal representative of movement of a patient from a movement sensor, determining the patient is inactive based on the movement signal over a moving time window, and initiating cardiac remodeling pacing in response to determining that the patient is inactive.

One illustrative cardiac remodeling pacing device may include a movement sensor to provide a movement signal representative of movement of a patient and a computing apparatus comprising one or more processors and operably coupled to the movement sensor. The computing apparatus may be configured to receive the movement signal from the movement sensor, determine the patient is inactive based on the movement signal over a moving time window, and initiate cardiac remodeling pacing in response to determining that the patient is inactive.

One illustrative cardiac remodeling pacing device may include a movement sensor to provide a movement signal representative of movement of a patient and a computing apparatus comprising one or more processors and operably coupled to the movement sensor. The computing apparatus may be configured to receive the movement signal from the movement sensor, generate a weighted activity level for each time segment of a moving time window based on the movement signal, determining that the patient is inactive using the weighted activity level for the moving time window, and initiate cardiac remodeling pacing in response to determining that the patient is inactive.

The above summary is not intended to describe each disclosed embodiment or every implementation of the present disclosure. The figures and the detailed description below more particularly exemplify illustrative embodiments.

BRIEF DESCRIPTION OF THE DRAWINGS

The discussion below refers to the following figures, wherein the same reference number may be used to identify the similar/same component in multiple figures. However, the use of a number to refer to a component in a given figure is not intended to limit the component in another figure labeled with the same number. The figures are not necessarily to scale.

DETAILED DESCRIPTION

The techniques of this disclosure generally relate to heart failure and, in particular, to opportunistically determining and increasing time periods for providing cardiac remodeling pacing therapy to treat heart failure (HF). Heart failure patients, such as patients having heart failure with preserved ejection fraction (HFpEF), may be provided with cardiac therapy, such as pacing therapy, which may result in cardiac remodeling of the patient's heart. Cardiac remodeling may be beneficial in some cases or adverse in other cases. The present disclosure provides techniques for determining when to provide cardiac remodeling therapy, for example, during periods of low activity when the patient is at rest or minimally exerting themselves, at which periods cardiac remodeling pacing is indicated. This can allow therapy to be provided without causing symptoms during activities of daily living. Each of these therapies can be implemented with cardiac therapy systems and devices as described further below.

Figure 1:
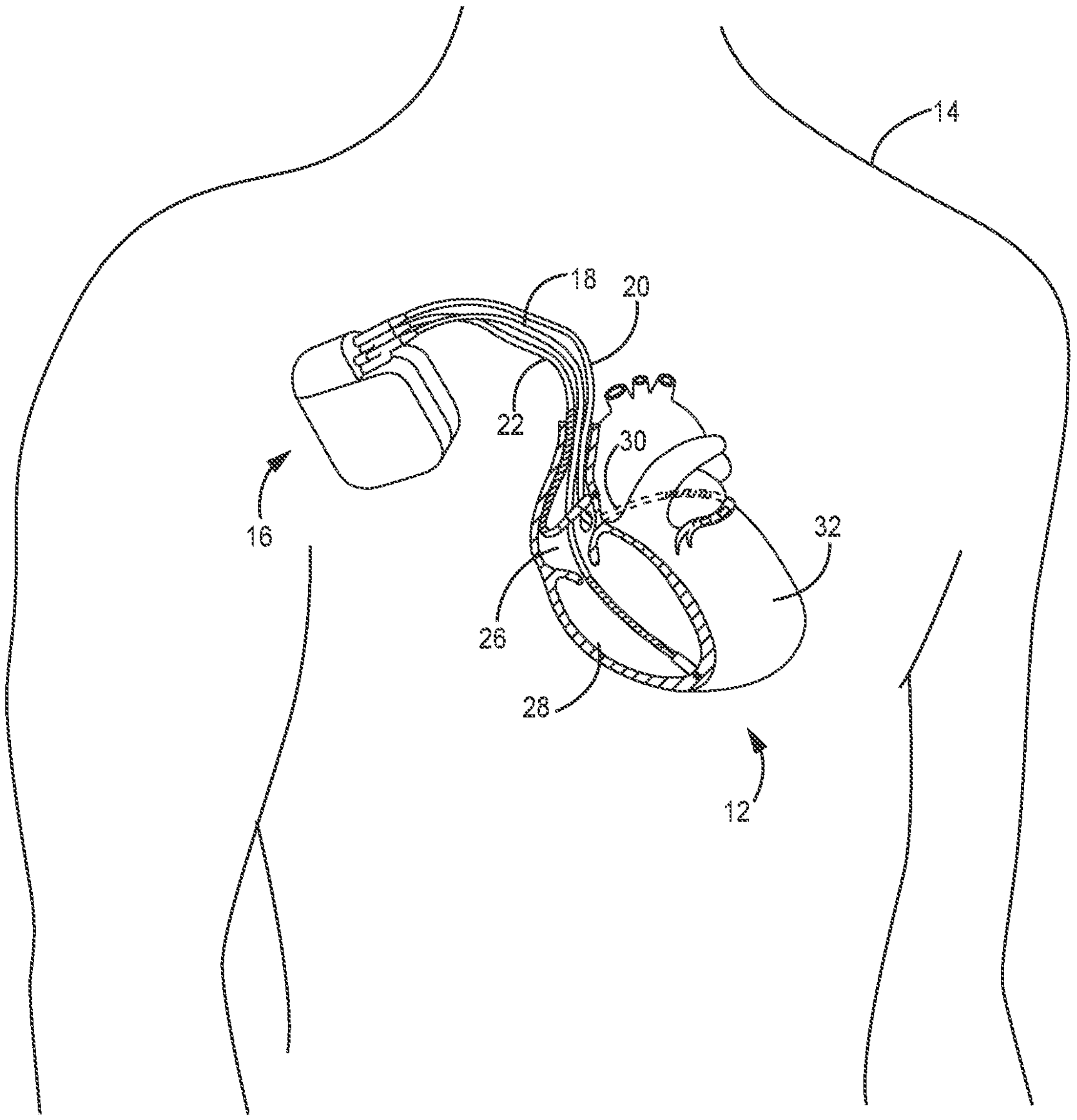
FIG. 1 is a diagram of a system including an IMD, in accordance with various embodiments described herein.

FIG. 1 is a conceptual diagram of an exemplary therapy system 10 that may be used to deliver pacing therapy, such as cardiac remodeling pacing therapy, to a patient 14. While patient 14 is shown as a human, patient 14 may also be a variety of other types of animals. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pacing rate, R-R interval, A-V delay and other various timings, pulse width, amplitude, voltage, burst length, etc. Further, the IMD 16 may be operable to use various electrode configurations to deliver pacing therapy, which may be unipolar, bipolar, quadripolar, or further multipolar. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD, or electrode apparatus. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of the heart 12 is stopped.

Figure 2:
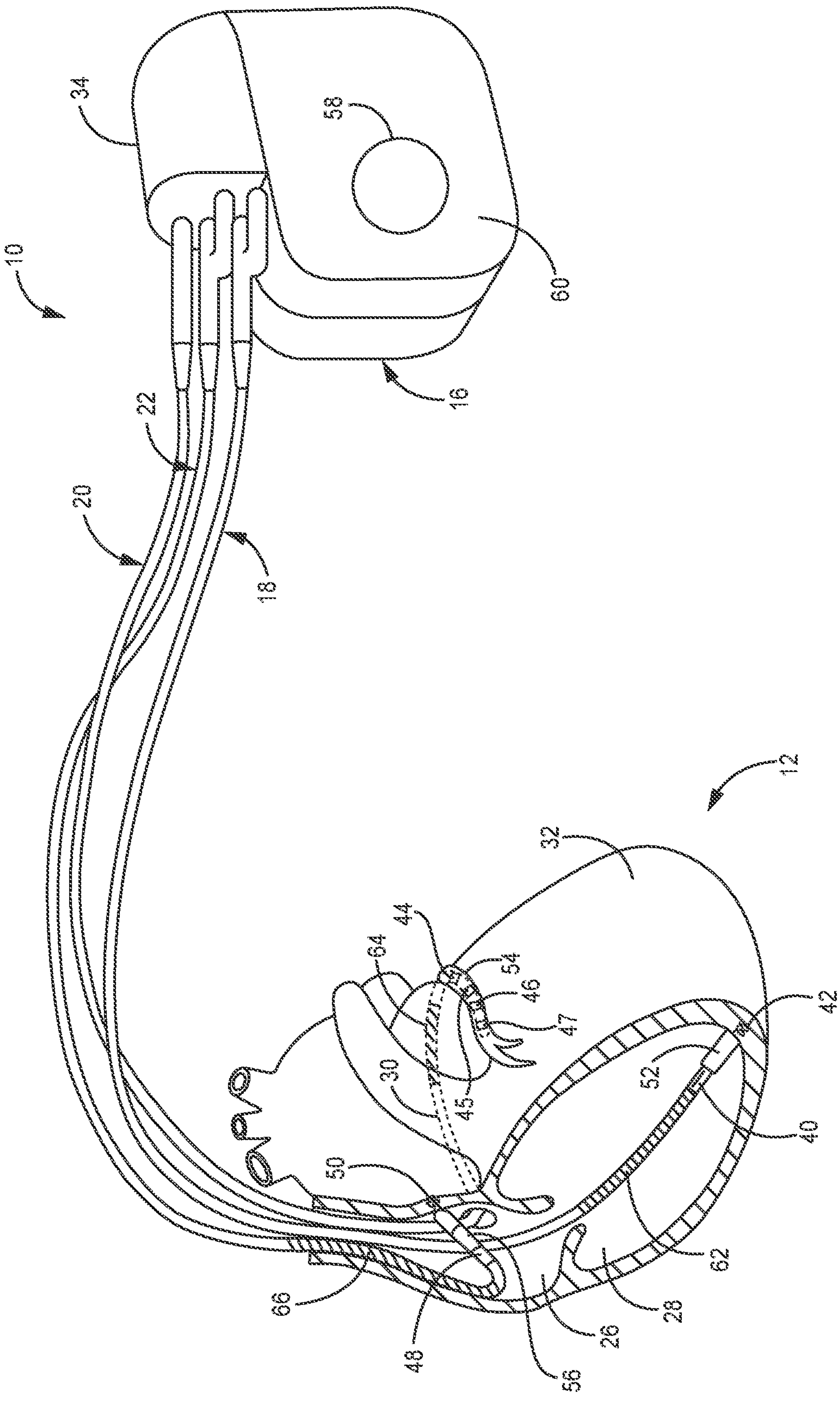
FIG. 2 is a diagram of the IMD of FIG. 1.

FIG. 2 is a conceptual diagram of the IMD 16 and the leads 18, 20, 22 of therapy system 10 of FIG. 1 in more detail. The leads 18, 20, 22 may be electrically coupled to a therapy delivery module (e.g., for delivery of cardiac remodeling pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 2, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The above-described configuration of the therapy system 10 is merely one example. In other examples, the therapy system may include epicardial leads and/or patch electrodes instead of, or in addition to, the transvenous leads 18, 20, 22 illustrated in FIG. 1. In further embodiments, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 1). In one example, the left ventricular (LV) coronary sinus lead 20 extends through one or more veins, the vena cava, the right atrium 26, and into the coronary sinus 30 to a region adjacent to the free wall of the left ventricle 32 of the heart 12. Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

Other example therapy systems that provide electrical stimulation therapy to the heart 12 may include any suitable number of leads coupled to the IMD 16, and each of the leads may extend to any location within or proximate to the heart 12. Such other therapy systems may include three transvenous leads located as illustrated in FIGS. 1-2. Still further therapy systems may include a single lead that extends from the IMD 16 into the right atrium 26 or two leads that extend into a respective one of the right atrium 26 and the left atrium. In one example, the IMD 16, as a cardiac resynchronization therapy (CRT) device with a left ventricular (LV) lead may be useful for a HFpEF patient if there is a complete AV node block, as a LV lead can be more beneficial than a RV lead in such patients. In some examples, it can be desirable to deliver rate responsive pacing to the atrium for a HFpEF patient with chronotropic incompetence with an atrial lead (i.e., single chamber atrial system such as AAI) and atrial and ventricular lead system (i.e., dual chamber system such as DDD and VDD).

Figure 3A:
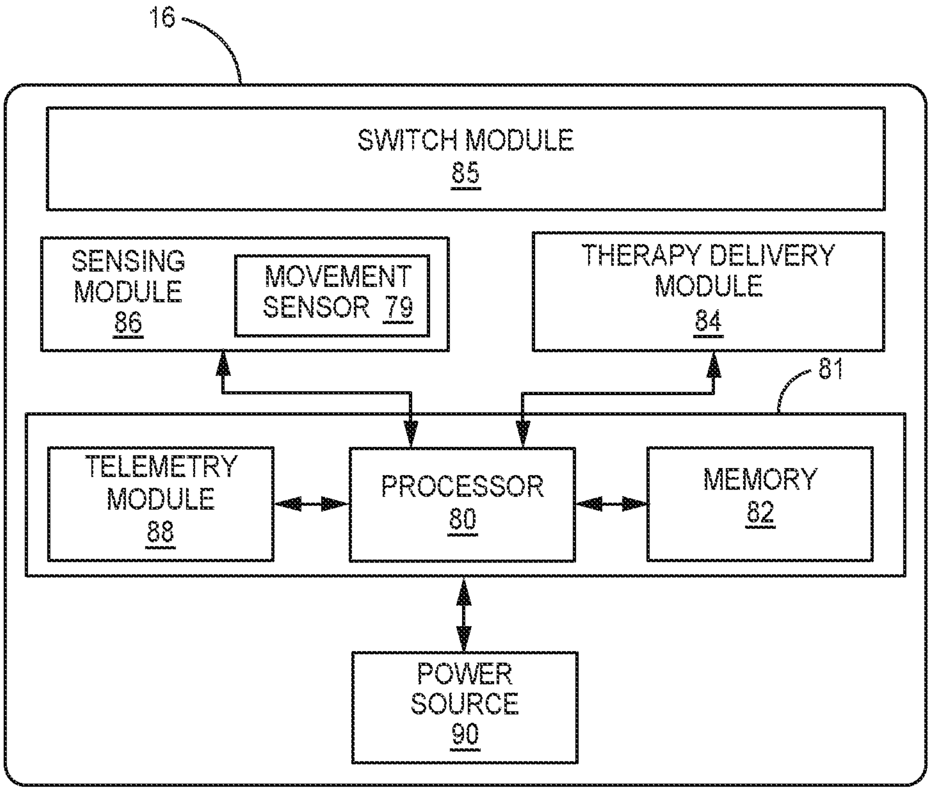
FIG. 3A is a block diagram of an IMD, e.g., of the systems of FIGS. 1-2, in accordance with embodiments described herein.

FIG. 3A is a functional block diagram of an example configuration of the IMD 16. As shown, the IMD 16 may include a control module 81, a therapy delivery module 84 (e.g., which may include a stimulation generator), a sensing module 86, and a power source 90. The control module, or apparatus, 81 may include a computing apparatus 80, memory 82, and a telemetry module, or apparatus, 88. The memory 82 may include computer-readable instructions that, when executed, e.g., by the computing apparatus 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically erasable programmable ROM (EEPROM), flash memory, and/or any other digital media.

The computing apparatus 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the computing apparatus 80 may include multiple components, such as any combination of one or more microprocessors, one or more controllers, one or more DSPs, one or more ASICs, and/or one or more FPGAs, as well as other discrete or integrated logic circuitry. The functions attributed to the computing apparatus 80 herein may be embodied as software, firmware, hardware, or any combination thereof.

The control module 81 may control the therapy delivery module, or apparatus, 84 to deliver therapy (e.g., electrical stimulation therapy such as cardiac remodeling pacing) to the heart 12 according to a selected one or more therapy programs, which may be stored in the memory 82, and based on algorithms, or methods, described further below. More, specifically, the control module 81 (e.g., the computing apparatus 80) may control various parameters of the electrical stimulus delivered by the therapy delivery module 84 such as, e.g., A-V delays, pacing pulses with the amplitudes, pulse widths, frequency, or electrode polarities, etc., which may be specified by one or more selected therapy programs (e.g., A-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, the therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to the heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured to deliver one or more of these types of stimulation in the form of other signals, such as sine waves, square waves, and/or other substantially continuous time signals.

The IMD 16 may further include a switch module, or apparatus, 85 and the control module 81 (e.g., the computing apparatus 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module, or apparatus, 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switch module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt-driven device and may be responsive to interrupts from pacer timing and control module, where the interrupts may correspond to the occurrences of sensed P-waves and R-waves and the generation of cardiac pacing pulses. Any necessary mathematical calculations may be performed by the computing apparatus 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the computing apparatus 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the computing apparatus 80, the telemetry module 88 may receive downlink telemetry from and send uplink telemetry to a programmer with the aid of an antenna, which may be internal and/or external. The computing apparatus 80 may provide the data to be uplinked to a programmer and the control signals for the telemetry circuit within the telemetry module 88, e.g., via an address/data bus. In some examples, the telemetry module 88 may provide received data to the computing apparatus 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 3B:
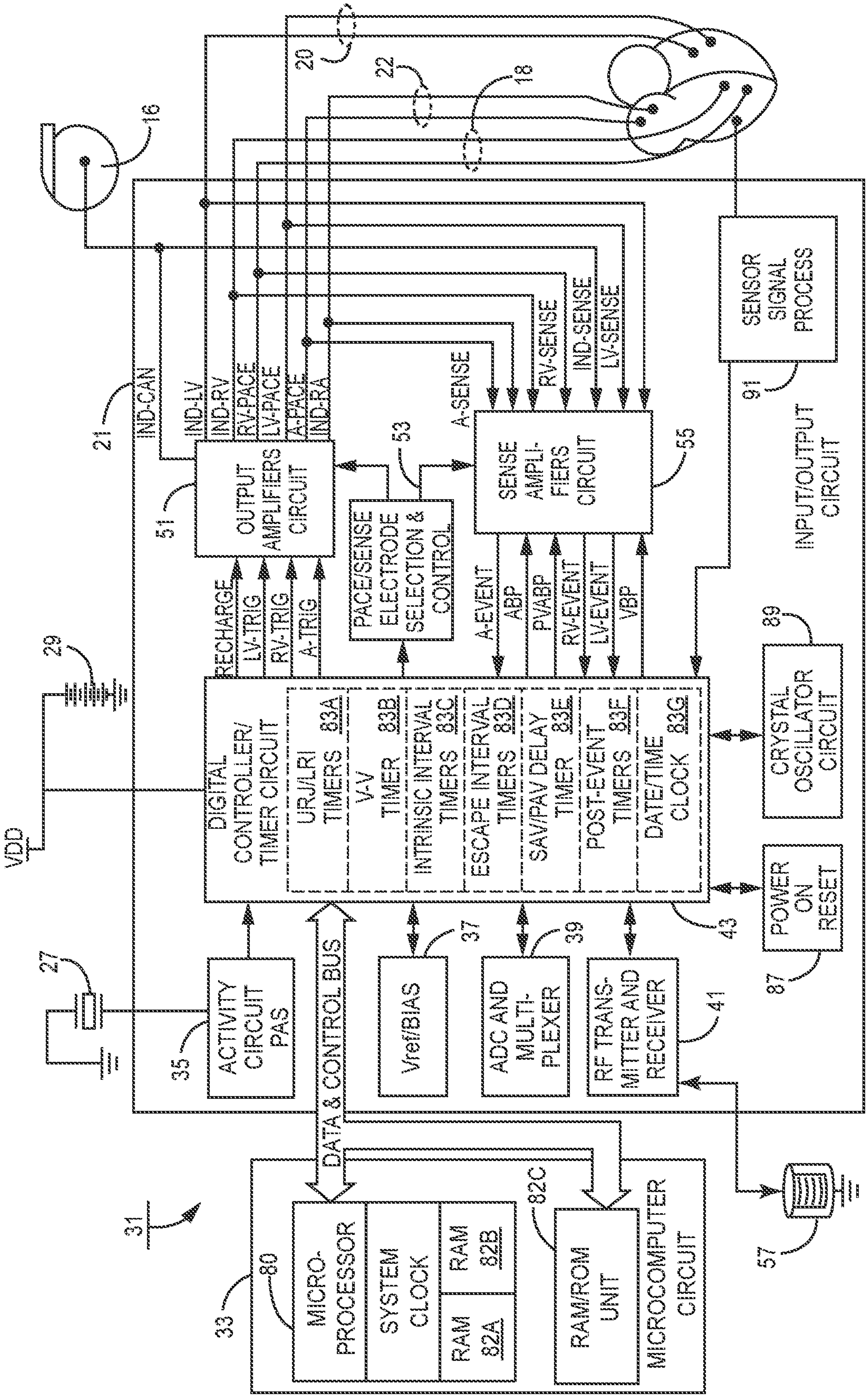
FIG. 3B is another block diagram of IMD circuitry and associated leads employed in the systems of FIGS. 1-2.

FIG. 3B is a functional block diagram for an embodiment of IMD 16 that depicts bipolar RA lead 22, bipolar RV lead 18 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the digital controller/timer circuit 43 via data and control bus to microcomputer circuitry 33. The IPG circuit 31 is illustrated in a functional block diagram divided generally into the microcomputer circuitry 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Voltage reference and bias circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers circuit 55 for uplink transmission via RF telemetry transceiver 41. Voltage reference and bias circuit 37, ADC and multiplexer circuit 39, power-on-reset circuit 87, and crystal oscillator circuit 89 may correspond to any of those used in illustrative implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the activity circuit (patient activity sensor (PAS)) 35 in the example IPG circuit 31. The patient activity sensor 27 is coupled to the IPG housing and may take the form of a piezoelectric crystal transducer. The output signal of the patient activity sensor 27 may be processed and used as an RCP. Sensor 27 generates electrical signals in response to sensed physical activity that are processed by activity circuit 35 and provided to digital controller/timer circuit 43. Similarly, the illustrative systems, apparatus, and methods described herein may be practiced in conjunction with alternate types of sensors such as oxygenation sensors, pressure sensors, pH sensors, temperature sensors, respiration sensors, perfusion sensors, heart sound sensors, and heart rate sensors, for use in providing rate responsive pacing capabilities. For example, impedance can be measured using a ring electrode on the lead (e.g., RA or RV lead) and temperature can be measured by a sensor at the distal end of the lead. Alternately, QT time may be used as a rate indicating parameter, in which case no extra sensor is required. Similarly, the illustrative embodiments described herein may also be practiced in non-rate responsive pacemakers.

Data transmission to and from the external programmer is accomplished by way of the telemetry antenna 57 and an associated RF telemetry transceiver 41, which serves both to demodulate received downlink telemetry and to transmit uplink telemetry. Uplink telemetry capabilities may include the ability to transmit stored digital information, e.g., activity information, rate responsive pacing profiles, operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer circuitry 33 contains a computing apparatus 80 and associated system clock and on-processor RAM and ROM chips 82A and 82B, respectively. In addition, microcomputer circuitry 33 includes a separate RAM/ROM chip 82C to provide additional memory capacity. Computing apparatus 80 normally operates in a reduced power consumption mode and is interrupt driven. Computing apparatus 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuitry 33 by way of data and control bus from programmed-in parameter values and operating modes. In addition, if programmed to operate as a rate responsive pacemaker, a timed interrupt, e.g., every cycle or every two seconds, may be provided to allow the microprocessor to analyze the activity sensor data and update the basic pacing rate as well as A-A, V-A, as applicable. In addition, the computing apparatus 80 may also serve to define variable, operative A-V delay intervals, and the energy delivered to each ventricle and/or atrium.

In one embodiment, computing apparatus 80 is a custom microprocessor adapted to fetch and execute instructions stored in RAM/ROM memory 82 in a conventional manner. It is contemplated, however, that other implementations may be suitable to practice the disclosed methods. For example, an off-the-shelf, commercially available microprocessor or microcontroller, or custom application-specific, hardwired logic, or state-machine type circuit may perform the functions of computing apparatus 80.

Digital controller/timer circuit 43 operates under the general control of the microcomputer circuitry 33 to control timing and other functions within the pacing circuit 21 and includes a set of timing and associated logic circuits of which certain ones pertinent to the present disclosure are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals, escape interval timers 83D for timing A-A, and/or V-A pacing escape intervals, an A-V delay interval timer 83E for timing the A-LVp delay (or A-RVp delay) from a preceding A-EVENT or A-TRIG, a post-ventricular event timer 83F for timing post-ventricular time periods, and a date/time clock 83G.

The A-V delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery and can be based on one or more prior cardiac cycles (or from a data set empirically derived for a given patient).

The post-ventricular event timer 83F times out the post-ventricular period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer circuitry 33. The post-ventricular time periods include a post-ventricular atrial blanking period (PVARP), a post-atrial ventricular blanking period (PAVBP), a ventricular blanking period (VBP), and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The computing apparatus 80 also optionally calculates A-V delays, post-ventricular time periods, and post-atrial time periods that vary with the sensor-based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. To trigger generation of an RV-PACE or LV-PACE pulse, digital controller/timer circuit 43 may utilize the algorithms described below.

The output amplifiers circuit 51 includes switching circuits for coupling selected pace electrode pairs from among the lead conductors and the IND-CAN electrode to the RA pace pulse generator (and LA pace pulse generator if provided), RV pace pulse generator and LV pace pulse generator. Pace/sense electrode selection and control circuit 53 selects lead conductors and associated pace electrode pairs to be coupled with the atrial and ventricular output amplifiers within output amplifiers circuit 51 for accomplishing RA, LA, RV, and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers circuit 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory and can inadvertently be triggered by electrical noise signals or aberrantly conducted depolarization waves rather than true R-waves or P-waves.

The techniques described in this disclosure, including those attributed to the IMD 16 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

The systems, devices, and methods described herein may be used to determine and adjust a cardiac remodeling pacing therapy for HFpEF patients, as described further herein. An increase in heart rate can lead to left ventricle wall thinning and dilatation. Myocyte cell loss and myocyte reactive hypertrophy may be major components of ventricular remodeling in pacing-induced dilated cardiomyopathy. Such cardiac remodeling may be desirable for patients with HFpEF since they have a normal size ventricle with an increased wall thickness.

Several different pacing therapies may be used for treating HFpEF such as, e.g., atrioventricular node stimulation (AVNS) to reduce ventricular rate during atrial fibrillation, atrial pacing and rate adaptive pacing, nocturnal overdrive pacing, PR interval optimization by ventricular pacing, and AVNS to decrease inflammation. Nocturnal overdrive pacing, e.g., increasing the heart rate (i.e., tachycardia pacing), may cause remodeling in a hypertrophic swine model with rate-dependent LV chamber volume expansion and increased compliance. Details regarding cardiac remodeling pacing may be further provided in U.S. Patent Application Publication No. 2019/0381323A1 entitled "Delivery of Cardiac Pacing Therapy for Cardiac Remodeling" and published on Dec. 19, 2019, which is herein incorporated by reference in its entirety.

Opportunistic high-rate pacing during the day while maintaining high-rate pacing at night may also be utilized. For example, higher rate (e.g., higher than 100 beats per minute, or at least 110 beats per minute) of pacing can be provided for longer periods (e.g., more than five hours or at least six hours) of time during times of low activity (e.g., at night) and additionally other opportunistic pacing can be provided during the day, for a total more than ten hours (e.g., about 12 hours) of pacing therapy. However, inappropriate daytime high-rate pacing (e.g., about 100-130 beats per minute) may cause symptoms including palpitations, exertional shortness of breath, and hypotension.

Figure 4:
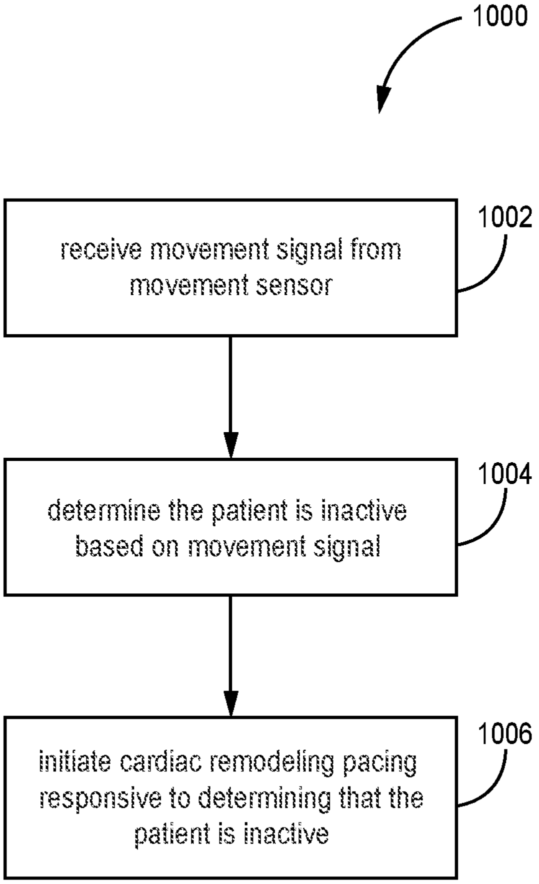
FIG. 4 is a flow diagram that illustrates one example of a method of performing cardiac remodeling pacing.

An illustrative cardiac remodeling pacing method 1000 is depicted in FIG. 4. The method 1000 can be performed by the computing apparatus 80, movement sensor 79, and any other element or portion of the IMD 16 described herein with reference to FIGS. 1-3. It is to be understood that the illustrative method 1000 and processes described therein may be performed on non-implantable devices or subdermal implanted devices, which may communicate with pacing devices to deliver the cardiac remodeling pacing. For example, the illustrative method 100 may be performed by an external device (e.g., outside of the patient's body) but may communicate with an IMD to deliver the cardiac remodeling pacing.

The method 1000 includes receiving a movement signal from a movement sensor 1002. The movement sensor signal may be provided by a movement sensor such as, for example, the movement sensor 79 of sensing module 86 of IMD 16 shown in FIG. 3A. The movement sensor can include a single-axis piezoelectric accelerometer in the antero-posterior (AP) direction. In some devices, a three-axis accelerometer can be used, in which case only inputs from one axis (e.g., the AP axis) may be used. The movement signal may be representative of movement of the patient.

The method 1000 further includes determining that the patient is inactive based on the movement signal over a moving time window 1004. Thus, the movement signal may be analyzed over a moving, or sliding, time window to determine whether the movement signal within the moving, or sliding, time window is indicative of the patient being inactive. In other words, the movement signal within the moving time window may reflect the immediately previous time period of movement of the patient. In this way, the patient's most recent activity may be analyzed to determine whether the patient is inactive.

The moving time window may between about 30 seconds and about 15 minutes. In at least one embodiment, the moving time window may be 30 seconds. In at least one embodiment, the moving time window may be six minutes. Further, the moving time window may be greater than or equal to 30 seconds, greater than or equal to 45 seconds, greater than or equal to 1 minute, greater than or equal to 2 minutes, greater than or equal to 3 minutes, greater than or equal to 5 minutes, etc. and/or less than or equal to 15 minutes, less than or equal to 10 minutes, less than or equal to 8 minutes, less than or equal to 6 minutes, less than or equal to 4 minutes, less than or equal to 180 seconds, etc.

Additionally, the moving time window may be adjusted, or modified, during the operation, or the running, of method 1000. For example, the length of the moving time window may be adjusted in response to movement patterns being detected. For example, the window duration may be extended when the gaps between movement detections are within a selected percentage, e.g., 20%, of the total window duration.

If the patient is inactive, it may be an appropriate time to deliver cardiac remodeling pacing. Thus, in response to determination that the patient is inactive 1004, the method 1000 may initiate cardiac remodeling pacing therapy 1006. Cardiac remodeling pacing may be described in more detail in U.S. Pat. App Pub. No. 2019/0381322 entitled "Delivery of Cardiac Pacing Therapy for Cardiac Remodeling" and published on Dec. 19, 2019, to Sharma et al., which is incorporated by reference herein in its entirety. In one or more embodiments, upon initiation of the cardiac remodeling pacing, the pacing rate may be increased over an acceleration time period until the pacing rate reaches the desired cardiac remodeling pacing rate. Additionally, in one or more embodiments, upon termination or cessation of the cardiac remodeling pacing (e.g., due to a determination that the patient is active as described herein, due to the cardiac remodeling pacing treatment being completed, etc.), the pacing rate of the cardiac remodeling pacing may be decreased over a deceleration time period until the pacing rate returns to the standard rate or the pacing therapy ceases.

Figure 5:
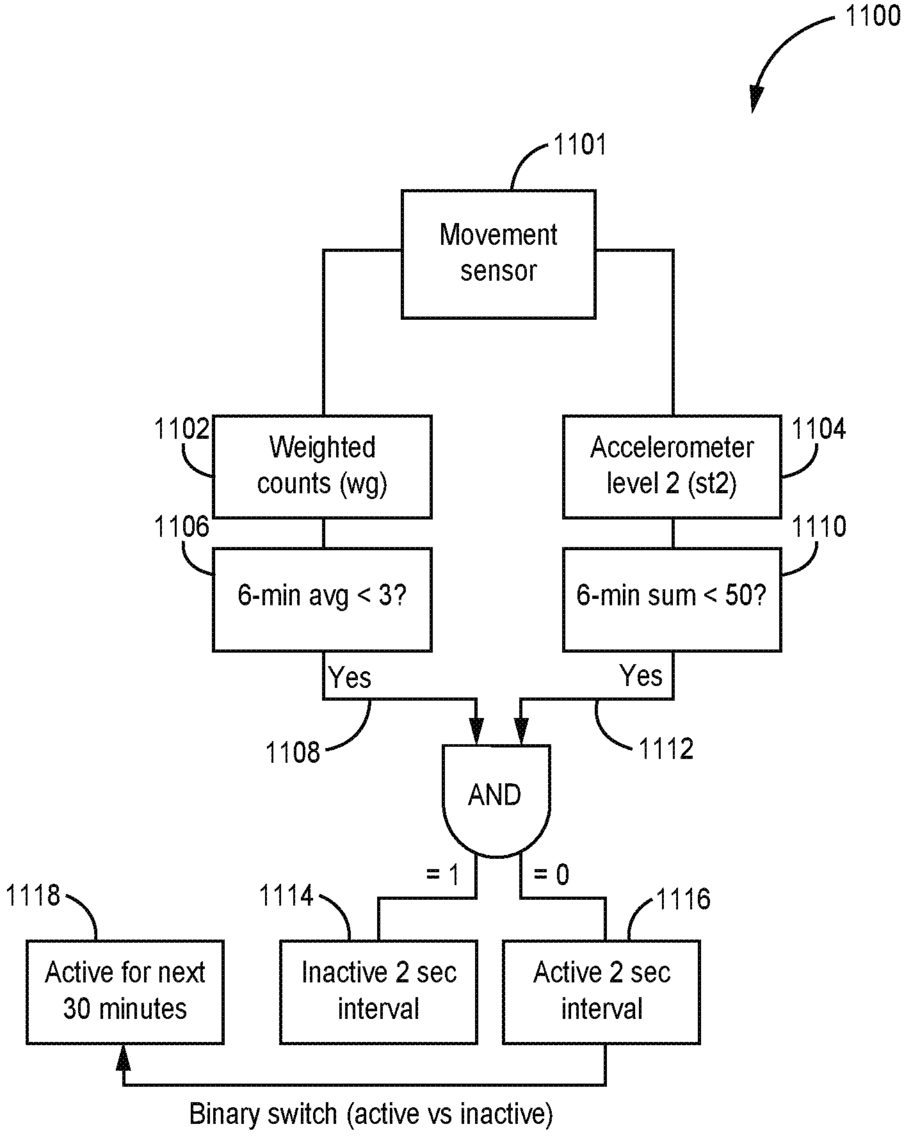
FIG. 5 illustrates an illustrative low activity detection algorithm in accordance with embodiments.

Determination of whether a patient is inactive based on the movement signal may be performed using multiple illustrative processes. One illustrative method 1110 of determining that a patient is inactive based on the movement signal is depicted in FIG. 5. The method 1100 can be executed by the computing apparatus 80 and any other element or portion of the IMD 16. The method 1100 utilizes the movement signal provided by the movement sensor 1101, and as shown, performs two different processes with respect to the movement signal to determine whether the patient is inactive. Although the illustrative method shows two processes performed on the movement signal to determine whether the patient is inactive, it is to be understood that only one of the two processes may be utilized or performed by the illustrative methods and devices described herein to determine whether a patient is active or inactive. In particular, the first inactivity determination process may be described as a weighted activity level process that is depicted on the left side of FIG. 5 between the movement sensor 1101 and the "AND" and includes processes 1102, 1106. Further, the second inactivity determination process may be described as a non-weighted inactivity process that is depicted on the right side of FIG. 5 between the movement sensor 1101 and the "AND" and includes processes 1104, 1110. Thus, an illustrative inactivity determination method for use with the cardiac remodeling pacing described herein may only include or utilize processes 1102, 1106 and/or processes 1104, 1110. In such embodiments where only one of the two described processes is utilized, the "AND" portion of method 1110 would not be utilized. Additionally, as shown, the illustrative inactivity determination method 1100 for use with the cardiac remodeling pacing includes both sets of processes 1102, 1106 and processes 1104, 1110, with their outputs being "joined" as described herein.

Figure 6:
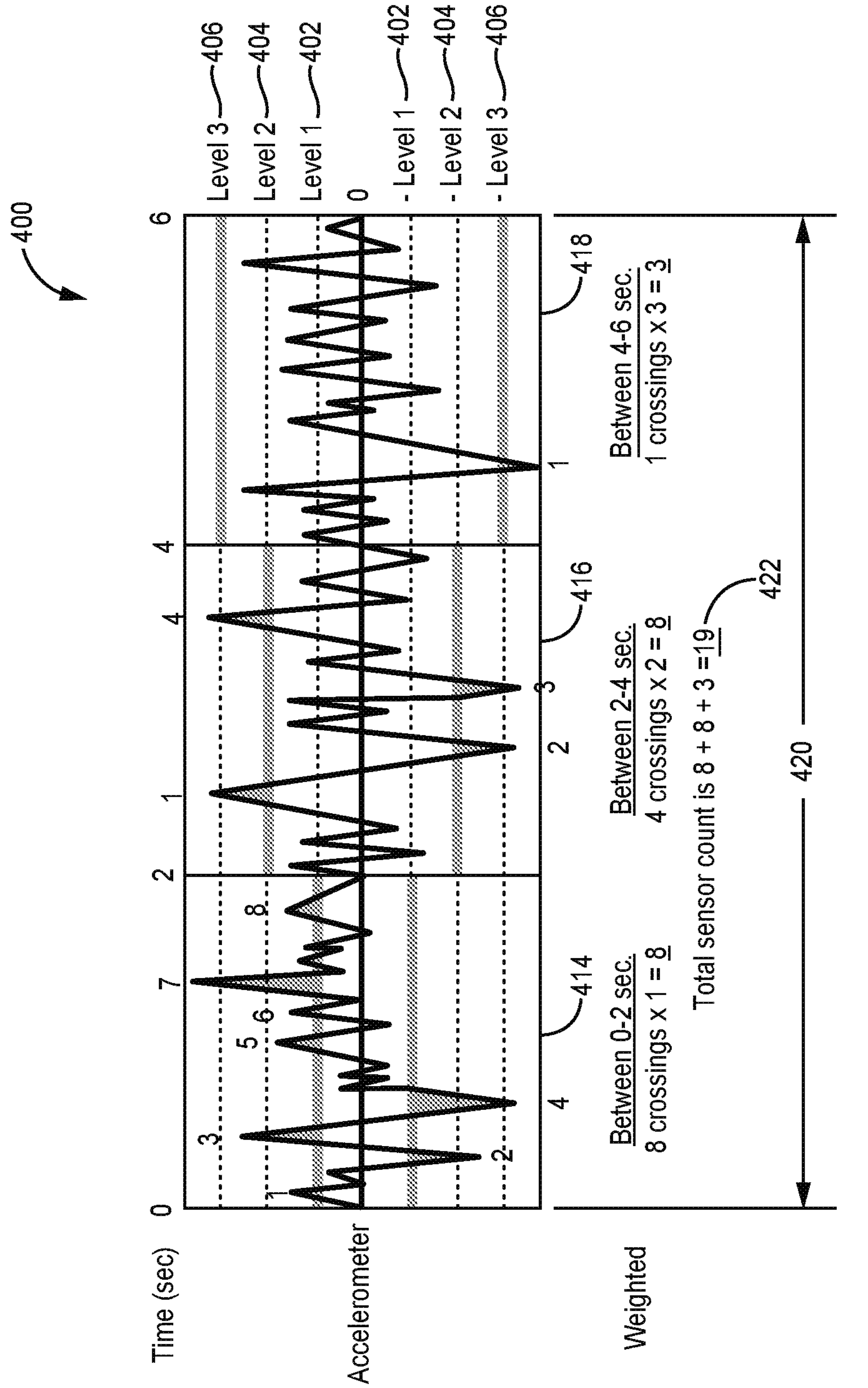
FIG. 6 illustrates sensor count measurement using a plurality of sensitivity levels in accordance with embodiments.

A weighted activity level 1102 may be generated or created using the movement signal as described herein with more detail with respect to the FIG. 6. A movement signal is depicted plotted over a time segment 420. The moving time window described herein may include a plurality of consecutive time segments 420. Each time segment may include a plurality of consecutive time portions. In this example, the time segment 420 includes a first time portion 414, a second time portion 416, and a third time portion 418. As shown, the time segment 420 is 6 seconds, and each consecutive time portion is 2 seconds. The time segment 420 may between about 2 seconds and 30 seconds, and each consecutive time portion may be between about 0.5 seconds and 10 seconds. Further, although as shown each consecutive time portion is equal, the consecutive time portions of time segments in other embodiments may not be equal (e.g., depending on the threshold level used within the time portion as will be described further herein).

The movement signal may be analyzed differently within each time portion to provide the weighted activity level. For example, a plurality of different threshold levels may be defined, and each different threshold level may correspond to a different consecutive time portion of the time segment. In this particular example, three different threshold levels are utilized, namely "Level 1" 402, "Level 2" 404, and "Level 3" 406. "Level 1" 402 may be the most sensitive to activity, "Level 3" 406 may be the least sensitive to activity, and "Level 2" 404 may be less sensitive than "Level 1" 402 and more sensitive than "Level 3" 406 to activity. In other words, the sensitivity of threshold levels may extend from least sensitive to most sensitivity to activity. In at least one embodiment, the "Level 1" 402 may be 0.1 the acceleration of gravity (g), "Level 2" 404 may be 0.2 g, and "Level 3" 406 may be 0.4 g. Furthermore, the threshold levels may be configurable or adjustable based on one or more patient characteristics, for instance, during device configuration by a clinician either immediately after implantation or during later adjustment.

Additionally, each threshold level is an absolute value or amplitude. In other words, whether the movement signal is positive or negative does not matter; only the magnitude of the movement signal is evaluated using the threshold levels.

Each threshold level may be associated with or correspond to a different consecutive time portion and may be utilized to evaluate the movement signal during the associated or corresponding time portion. In one or more embodiments, a number of times that the movement signal crosses the corresponding threshold level after crossing zero for each of the plurality of consecutive time portions of the time segment may be determined. For example, during time portion 414, the threshold "Level 1" 402 is utilized and the movement signal is determined to cross the threshold "Level 1" 402 8 times (in other words, "8 crossings"). It is be understood that although the movement signal does marginally cross the threshold "Level 1" 402 twice between crossing "7" and "8," such crossings are not counted or realized because the movement signal did not cross zero before increasing to the cross the threshold "Level 1" 402. Further, for example, during time portion 416, the threshold "Level 2" 404 is utilized and the movement signal is determined to cross the threshold "Level 2" 404 4 times (in other words, "4 crossings"). Still further, for example, during time portion 418, the threshold "Level 3" 406 is utilized and the movement signal is determined to cross the threshold "Level 3" 406 1 times (in other words, "1 crossing"). The weighted activity level 422 for the time segment 420 may then be generated based on each of the number of times the movement signal crossed the thresholds (i.e., the "crossings").

The weighted activity level 422 is "weighted," which generally means that crossings of each different time portion and different threshold may be given a different significance or weight. In one embodiment, a weight associated with each of the plurality of threshold levels may be defined. For example, and as shown, the time portion 414 and the threshold "Level 1" 402 may define, or utilize, a weight of "1," the time portion 416 and the threshold "Level 2" 404 may define, or utilize, a weight of "2," and the time portion 418 and the threshold "Level 3" 406 may define, or utilize, a weight of "3." A weighted activity level portion score may be generated for each of the plurality of consecutive time portions of the time segment based on the number of times that the movement signal crosses the corresponding threshold level for the consecutive time portion and the weight associated with the threshold level corresponding to the consecutive time portion. In one or more embodiments, the number of signal crosses may be multiplied by the corresponding weight. For example and as shown, the 8 crossings of the time portion 414 may be multiplied by the weight of "1" resulting in a weighted activity level portion score of 8, the 4 crossings of the time portion 416 may be multiplied by the weight of "2" resulting in a weighted activity level portion score of 8, and the 1 crossing of the time portion 418 may be multiplied by the weight of "3" resulting in a weighted activity level portion score of 3.

The weighted activity level 422 for each time segment of the moving time window may be generated based on the weighted activity level portion scores generated for the plurality of consecutive time portions of the time segment. In one or more embodiments, the weighted activity level 422 may be the sum of the weighted activity level portions of the time segment 420. In this example depicted in FIG. 6, the weighted activity level is 19.

It is to be understood that the weighted activity level 1102 process may be performed continuously on the movement signal over time resulting in a string of weighted activity levels for each time segment.

The method 1100 may then use the generated weighted activity levels to determine whether the patient is inactive. In one or more embodiments, an activity level may be generated for the moving time window based on the generated weighted activity levels for the time segments of the moving time window, and then using the generated activity level, the method 1100 may determine whether the patient is inactive. For example, and as shown in FIG. 5, an average of the generated weighted activity levels over the moving time window of six minutes may be generated, and if the average is less than 3 1106, it may be determined that the patient is likely inactive 1108. More specifically, each time segment may have or correspond to a weighted activity level that is generated therefrom. Each of the weighted activity levels generated over the moving time window may be summed and then divided by the number of weighted activity levels generated during the moving time window to generate an average, which may be referred to as the activity level. If the average, or activity level, is less than 3 1106, it may be determined that the patient is likely inactive 1108.

A non-weighted activity level 1104 may also be generated or created using the movement signal. The non-weighted activity level may be generated by determining a number of times that the movement signal crosses a threshold level over the moving time window. In this example depicted in FIG. 5, the threshold level may be similar to the threshold "Level 2" 404 described with reference to FIG. 6. As such, the number of times that the movement signal crosses the threshold level over the moving time, which in this example is six minutes, may be counted or determined 1104. Then, if the non-weighted activity level is less than a non-weighted threshold value 1110, which in this example, is 50, then it may be determined that the patient is likely inactive 1112. The non-weighted threshold value may be between about 25 and 75; however, it is to be understood that such non-weighted threshold value may be a plurality of different values depending on the threshold level utilized and length of the moving time window.

As described herein, the method 1100 utilize two processes to determine whether the patient is inactive: the first inactivity determination process being the weighted activity level processes 1102, 1106; and the second inactivity determination process being non-weighted inactivity processes 1104, 1110. In this example, the method 1100 may only determine that the patient is inactive if both inactivity determinations 1108, 1112 are made (i.e., both processes determine that the patient is inactive) as depicted with the "AND" logic gate in FIG. 5. Thus, if both inactivity determinations 1108, 1112 determine that the patient is likely inactive, the method 1100 may determine that the patient is inactive 1114.

Otherwise, if only one of inactivity determinations 1108, 1112 determine that the patient is likely inactive, then method 1100 may determine that the patient is active 1116. In this example, the inactive designation 1114 may only be applied for a short time, and as shown, 2 seconds, before the method 1100 should re-evaluate the moving time window for activity or inactivity. In this way, the method 1100 may continuously being checking the patient for activity or inactivity.

Additionally, the active designation may be further applied for 30 minutes thereafter 1118. In other words, this method 1100 may be continuously running or looping to determine whether a patient is inactive or active but may pause and not determine whether a patient is active or inactive if the patient is determined to be active for a certain time period. The time period that the method 1100 is paused may be referred to a prevention time period or a hysteresis time period. As indicated in process 1118 shown in FIG. 5, the prevention time period may be 30 minutes.

Further, it is to be understood that additional criteria may be considered to confirm that the patient is active to move to process 1118 to enable to the prevention time period. In one or more embodiments, one or more metrics of the patient may be evaluated to confirm that the patient is active. For example, the patient's intrinsic heart rate may be monitored, and if the patient's intrinsic heart rate is greater than a threshold, then it may be determined that the patient is active and the method 1100 may move to process 1118. For instance, if the patient's intrinsic heart rate of the previous five-minute period is greater than or equal to 95 beats per minute (bpm), then it may be determined that the patient is active, and the prevention time period should be enabled 1118. Additionally, it to be understood that heart rate in combination with the movement signal described herein may also be used to determine whether a patient is inactive (e.g., below 50 bpm for 30 minutes may indicate inactivity).

In other words, after the patient is determined to be active over or during the moving time period, initiation of cardiac remodeling pacing may be restricted (e.g., blocked, stopped, etc.) for a prevention time period. The prevention time period may be between about 3 minutes and 180 minutes. In at least one embodiment, the prevention time period is 5 minutes. Further, the prevention time period may be greater than or equal to 1 minute, greater than or equal to 3 minutes, greater than or equal to 5 minutes, greater than or equal to 10 minutes, greater than or equal to 15 minutes, greater than or equal to 30 minutes, greater than or equal to 45 minutes, greater than or equal to 60 minutes, etc. and/or less than or equal to 180 minutes, less than or equal to 120 minutes, less than or equal to 75 minutes, less than or equal to 50 minutes, less than or equal to 40 minutes, less than or equal to 20 minutes, etc.

Additionally, the prevention time period may be modified during performance of the method 1100 based on various criteria. For example, a duration of activity may be monitored or determined, and the prevention time period may be modified, or adjusted, based on the duration of the activity. For instance, the prevention time period may be increased if the duration of the activity is determined to be longer than normal or typical. Likewise, the prevention time period may be decreased if the duration of the activity is determined to be shorter than normal or typical. Additionally, for example, the prevention time period may be modified or adjusted based on the time of day. For example, a patient may be presumed to be more active during the daytime and more likely to initiate activity during the daytime, and thus, the prevention time period may be increased during the daytime. Conversely, a patient may be presumed to be less active during the nighttime and less likely to initiate activity during the nighttime, and thus, the prevention time period may be decreased during the nighttime.

A trend of patient activity may be determined, or developed, based on historical patient activity that may be indicative of when a patient is more and less likely to be active and inactivation. Such trend of patient activity can then be used to modify or adjust the prevention time period. For example, if the trend of patient activity indicates a time period during which the patient is more active and more likely to initiate activity, then the prevention time period may be increased during such identified time period. Conversely, if the trend of patient activity indicates a time period during which the patient is less active and less likely to initiate activity, then the prevention time period may be decreased during such identified time period. Further, for example, if the trend of patient activity indicates a pattern of movement that is more likely to result in a longer duration of activity than normal or typical, then the prevention time period may be increased based on such pattern of movement. Conversely, if the trend of patient activity indicates a pattern of movement that is more likely to result in a shorter duration of activity than normal or typical, then the prevention time period may be decreased based on such pattern of movement.

Additionally, if the patient is determined to be active during the delivery of cardiac remodeling pacing, then the delivery of the cardiac remodeling pacing may be terminated (e.g., stopped, paused, cancelled, etc.). Then, the illustrative methods and processes described herein may continue running (e.g., looping, monitoring, etc.) to determine whether the patient is inactive before initiating cardiac remodeling pacing again.

Figure 7:
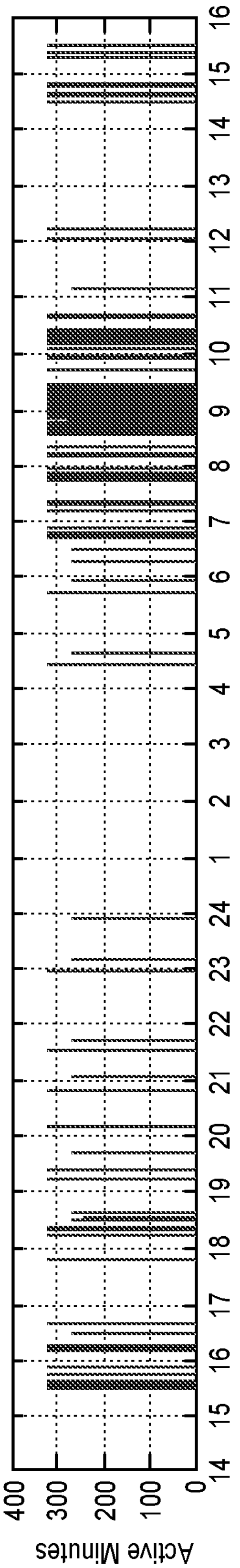
FIG. 7 illustrates historical activity level data for an HFpEF patient.

As described herein, thresholds, requirements, and time frames may be defined for determining an active period, and other values for each patient, based on historical activity level data for that patient. FIG. 7 illustrates historical activity level data for an HFpEF patient. The historical activity level data can be generated based on a movement signal, for example. The historical activity level data shown in FIG. 7 depicts activities over about 26 hours, for example from about 2 PM to about 4 PM. While a 26-hour chart is provided in FIG. 7, it will be appreciated that additional or less data can be captured.

Referring to FIG. 7, chart 500 illustrates portions in which the computing apparatus 80 determines that the patient is active. Some available algorithms for determining activity level based on a movement signal can detect periods of low activity when, in fact, therapy could be provided during that time without inducing adverse symptoms in the patient. For example, referring to chart 500, a patient may be relatively inactive, yet labeled as active, at various points from hour 17 (e.g., 5 PM) to hour 6 (e.g., 6 AM). By implementing algorithms and methods in accordance with embodiments, it may be determined to provide therapy during hours in which therapy would not have been provided using example methods described briefly earlier herein. In other words, algorithms in accordance with embodiments may provide therapy over a greater number of hours, leading to improved cardiac remodeling for HFpEF patients, relative to available methods and algorithms.

As mentioned earlier herein, one or more illustrative methods and algorithms determine whether a patient is active by summing weighted movement sensor counts for one minute. In one or more embodiments, the criteria for determining when a patient is active by summing weighted and rotated activity counts for more than a minute may be redefined or modified. In other words, an active period can be redefined as a period of more than one minute. For example, it may not be determined that a patient is active unless the patient is active for at least 2 minutes, or for at least 6 minutes, or for another physiologically significant time frame. The patient may then be considered inactive (and therapy can be provided) over larger amounts of time throughout a day, leading to improved patient outcomes.

The physiologically significant time frame can be determined based on differences between HFpEF patients and healthy people. In healthy people, levels of activity can be described by metabolic demand and a distinction between low and medium activity can be defined in terms of metabolic equivalents (METs). For example, a distinction between low and medium activity for healthy patients can occur at about 3 METs, corresponding to walking 3 miles per hour (mph) for most healthy patients. In contrast, HFpEF patients are symptom-limited, and a standard six-minute walk test (6 MWT) can bring HFpEF patients to an exertional state. Accordingly, any detected activity level that persists for less than this amount of time may not necessarily be a level at which pacing therapy would be contraindicated. The illustrative methods and devices described herein can use this information to provide pacing therapy until such a time as the patient becomes active for more than six minutes.

Furthermore, an exemplary HFpEF patient can be brought to an exertional state walking 2 mph during a 6 MWT. A typical motion sensor count at such a pace can be determined, and one or more of the thresholds (e.g., “Level 2” or medium sensitivity thresholds 404 of FIG. 6) can be set based on this study information. In some examples, the threshold value for process 1110 may be set to 50 counts or another value.

In addition to adjusting criteria for determining an "active period," or setting sensitivity thresholds, various pacing start and stop rules may be generated or determined, which define points at which pacing is started or stopped based on activity of the patient. A pacing start rule can be set the illustrative methods and processes are "slow" to label the patient inactive after a period of patient activity. This is equivalent to setting a hysteresis value such that pacing therapy is delayed somewhat once a patient's metabolic demand falls below a baseline. In some examples, the higher the activity level before the instant rest period, the more latency or hysteresis is provided before initiating overdrive pacing therapy during the instant rest period. A longer value for hysteresis (e.g., about 20-30 minutes, or below an upper limit of about 30 minutes) can provide increased specificity in the determination of low-activity states when there are short, repetitive motions interleaved with non-motion periods, and fewer false positives that can cause inappropriate overdrive pacing. A shorter hysteresis value (e.g., about 15-20 minutes, or a minimum of 15 minutes) can provide more opportunities to pace due to the longer cumulative inactive time of the patient.

A pacing stop rule can be set the cardiac remodeling pacing is quick to shut down overdrive pacing when activity is detected. In other examples, if intrinsic heart rate exceeds a paced rate, the cardiac remodeling pacing can shut down overdrive pacing.

By implementing methods in accordance with various embodiments, overdrive pacing can be provided for longer periods of time, leading to fewer missed opportunities for pacing and improved patient outcomes.

While the present disclosure is not so limited, an appreciation of various aspects of the disclosure will be gained through a discussion of the specific examples and illustrative embodiments provided below. Various modifications of the examples and illustrative embodiments, as well as additional embodiments of the disclosure, will become apparent herein.

ILLUSTRATIVE EXAMPLES

Example Ex1: A cardiac remodeling pacing method comprising:

- receiving a movement signal representative of movement of a patient from a movement sensor;
- determining the patient is inactive based on the movement signal over a moving time window; and
- initiating cardiac remodeling pacing in response to determining that the patient is inactive.

Example Ex2: A cardiac remodeling pacing device comprising:

- a movement sensor to provide a movement signal representative of movement of a patient; and
- a computing apparatus comprising one or more processors and operably coupled to the movement sensor, the computing apparatus configured to:
  - receive the movement signal from the movement sensor;
  - determine the patient is inactive based on the movement signal over a moving time window; and
  - initiate cardiac remodeling pacing in response to determining that the patient is inactive.

Example Ex3: The method or device as in any one of Examples Ex1-Ex2, wherein the moving time window is greater than or equal to 30 seconds.

Example Ex4: The method or device as in any one of Examples Ex1-Ex2, wherein the moving time window greater than or equal to six minutes.

Example Ex5: The method or device as in any one of Examples Ex1-Ex3, wherein the moving time window comprises a plurality of consecutive time segments, each time segment comprising a plurality of consecutive time portions, wherein determining a patient is inactive based on the movement signal over a moving time window comprises:

- defining a plurality of threshold levels, wherein each threshold level of the plurality of threshold levels is different and corresponds to a different one of the plurality of consecutive time portions of the time segment;
- determining a number of times that the movement signal crosses the corresponding threshold level for each of the plurality of consecutive time portions of the time segment;
- generating a weighted activity level for each time segment of the moving time window based on the determined number of times the movement signal crossed the corresponding threshold level for each of the plurality of consecutive time portions of the time segment; and
- determining that the patient is inactive using the weighted activity levels of the time segments of the moving time window.

Example Ex6: The method or device as in Example Ex5 wherein the plurality of threshold levels includes three or more threshold levels.

Example Ex7: The method or device as in any one of Examples Ex5-Ex6, wherein generating a weighted activity level for the time segment based on the determined number of times the movement signal crossed the corresponding threshold level for each of the plurality of consecutive time portions of the time segment comprises:

- defining a weight associated with each of the plurality of threshold levels;
- generating a weighted activity level portion score for each of the plurality of consecutive time portions of the time segment based on the number of times that the movement signal crosses the corresponding threshold level for the consecutive time portion and the weight associated with the threshold level corresponding to the consecutive time portion; and
- generating the weighted activity level for each time segment of the moving time window based on the weighted activity level portion scores generated for the plurality of consecutive time portions of the time segment.

Example Ex8: The method or device as in any one of Examples Ex5-Ex7, wherein determining a patient is inactive based on the movement signal over a moving time window comprises:

- generating an activity level for the moving time window based on the generated weighted activity levels for the time segments of the moving time window; and
- determining that the patient is inactive based on the generated activity level for the moving time window.

Example Ex9: The method or device as in Example Ex8, wherein the activity level for the moving time window is an average of the generated weighted activity levels for the time segments of the moving time window.

Example Ex10: The method or device as in any one of Examples Ex5-Ex9, wherein each time segment is greater than or equal to 6 seconds.

Example Ex11: The method or device as in any one of Examples Ex8-Ex10, wherein determining a patient is inactive based on the movement signal over a moving time window further comprises generating a non-weighted activity level for the moving time window, and wherein generating an activity level for the moving time window is further based on the generated non-weighted activity level for the moving time window.

Example Ex12: The method or device as in any one of Examples Ex1-Ex11, the method further comprising or the computing apparatus further configured to execute:

determining the patient is active over the moving time window; and restricting initiation of cardiac remodeling pacing in response to determining that the patient is active for a prevention time period.

Example Ex13: The method or device as in Example Ex12, wherein the prevention time period is greater than or equal to five minutes.

Example Ex14: The method or device as in any one of Examples Ex12-Ex13, the method further comprising or the computing apparatus further configured to execute:

determining a duration of activity; and modifying the prevention time period based on the duration of activity.

Example Ex15: The method or device as in any one of Examples Ex12-Ex14, the method further comprising or the computing apparatus further configured to execute: modifying the prevention time period based on a time of day.

Example Ex16: The method or device as in any one of Examples Ex12-Ex13, the method further comprising or the computing apparatus further configured to execute:

determining a trend of patient activity; and modifying the prevention time period based on the trend of patient activity.

Example Ex17: The method or device as in any one of Examples Ex1-Ex11, the method further comprising or the computing apparatus further configured to execute:

determining the patient is active over the moving time window; and terminating the cardiac remodeling pacing in response to determining that the patient is active.

Example Ex18: The method or device as in any one of Examples Ex12-Ex17, wherein the determining that the patient is active comprises determining that the patient's intrinsic heart rate is greater than a threshold heart rate.

Example Ex19: The method or device as in any one of Examples Ex17-Ex18, wherein terminating cardiac remodeling pacing in response to determining that the patient is active comprises decreasing a pacing rate of the cardiac remodeling pacing over a deceleration time period.

Example Ex20: The method or device as in any one of Examples Ex1-Ex19, the method further comprising or the computing apparatus further configured to execute: increasing a pacing rate of the cardiac remodeling pacing over an acceleration time period upon initiation thereof.

Example Ex21: The device as in any one of Examples Ex2-20, the device further comprising one or more pacing electrodes to deliver the cardiac remodeling pacing.

Example Ex22: A cardiac remodeling pacing device comprising:

a movement sensor to provide a movement signal representative of movement of a patient; and a computing apparatus comprising one or more processors and operably coupled to the movement sensor, the computing apparatus configured to:

receive the movement signal from the movement sensor;

generate a weighted activity level for each time segment of a moving time window based on the movement signal;

determining that the patient is inactive using the weighted activity level for the moving time window; and initiate cardiac remodeling pacing in response to determining that the patient is inactive.

Thus, various embodiments of methods for providing pacing in HFpEF pacing during periods of low activity are disclosed, e.g., during time windows for which cardiac remodeling pacing can be beneficial to the patient. Various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (for example, all described acts or events may not be necessary to carry out the techniques). In addition, while certain aspects of this disclosure are described as being performed by a single module or unit for purposes of clarity, the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

As used herein, the term "configured to" may be used interchangeably with the terms "adapted to" or "structured to" unless the content of this disclosure clearly dictates otherwise.

The singular forms "a," "an," and "the" encompass embodiments having plural referents unless its context clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

What is claimed is:

1. A cardiac remodeling pacing method comprising:

receiving a movement signal representative of movement of a patient from a movement sensor;

determining the patient is inactive based on the movement signal over a moving time window; and delivering cardiac remodeling pacing in response to determining that the patient is inactive, wherein the cardiac remodeling pacing comprises delivery of electrical stimulation to the patient's heart using one or more pacing electrodes to increase the patient's heart rate to lead to left ventricle wall thinning and dilation.

2. The method of claim 1, wherein the moving time window is greater than or equal to 30 seconds.

3. The method of claim 1, wherein the moving time window comprises a plurality of consecutive time segments, each time segment comprising a plurality of consecutive time portions, wherein determining a patient is inactive based on the movement signal over a moving time window comprises:

defining a plurality of threshold levels, wherein each threshold level of the plurality of threshold levels is different and corresponds to a different one of the plurality of consecutive time portions of the time segment;

determining a number of times that the movement signal crosses the corresponding threshold level for each of the plurality of consecutive time portions of the time segment;

generating a weighted activity level for each time segment of the moving time window based on the determined number of times the movement signal crossed the corresponding threshold level for each of the plurality of consecutive time portions of the time segment; and determining that the patient is inactive using the weighted activity levels of the time segments of the moving time window.

4. The method of claim 3, wherein generating a weighted activity level for the time segment based on the determined number of times the movement signal crossed the corresponding threshold level for each of the plurality of consecutive time portions of the time segment comprises:

defining a weight associated with each of the plurality of threshold levels;

generating a weighted activity level portion score for each of the plurality of consecutive time portions of the time segment based on the number of times that the movement signal crosses the corresponding threshold level for the consecutive time portion and the weight associated with the threshold level corresponding to the consecutive time portion; and generating the weighted activity level for each time segment of the moving time window based on the weighted activity level portion scores generated for the plurality of consecutive time portions of the time segment.

5. The method of claim 3, wherein determining a patient is inactive based on the movement signal over a moving time window comprises:

generating an activity level for the moving time window based on the generated weighted activity levels for the time segments of the moving time window; and determining that the patient is inactive based on the generated activity level for the moving time window.

6. The method of claim 5, wherein determining a patient is inactive based on the movement signal over a moving time window further comprises generating a non-weighted activity level for the moving time window, and wherein generating an activity level for the moving time window is further based on the generated non-weighted activity level for the moving time window.

7. The method of claim 1, the method further comprising:

determining the patient is active over the moving time window; and restricting initiation of cardiac remodeling pacing in response to determining that the patient is active for a prevention time period.

8. The method of claim 7, the method further comprising:

determining a duration of activity; and modifying the prevention time period based on the duration of activity.

9. The method of claim 8, the method further comprising one or more of:

modifying the prevention time period based on a time of day; and modifying the prevention time period based on a trend of patient activity.

10. The method of claim 1, the method further comprising:

determining the patient is active over the moving time window; and terminating the cardiac remodeling pacing in response to determining that the patient is active.

11. A cardiac remodeling pacing device for use with one or more pacing electrodes comprising:

a movement sensor to provide a movement signal representative of movement of a patient; and a computing apparatus comprising one or more processors and operably coupled to the movement sensor, the computing apparatus configured to:

receive the movement signal from the movement sensor;

determine the patient is inactive based on the movement signal over a moving time window; and deliver cardiac remodeling pacing in response to determining that the patient is inactive, wherein the cardiac remodeling pacing comprises delivery of electrical stimulation using the one or more pacing electrodes to the patient's heart to increase the patient's heart rate to lead to left ventricle wall thinning and dilation.

12. The device of claim 11, wherein the moving time window is greater than or equal to six minutes.

13. The device of claim 11, wherein the moving time window comprises a plurality of consecutive time segments, each time segment comprising a plurality of consecutive time portions, wherein determining a patient is inactive based on the movement signal over a moving time window comprises:

defining a plurality of threshold levels, wherein each threshold level of the plurality of threshold levels is different and corresponds to a different one of the plurality of consecutive time portions of the time segment;

determining a number of times that the movement signal crosses the corresponding threshold level for each of the plurality of consecutive time portions of the time segment;

generating a weighted activity level for each time segment of the moving time window based on the determined number of times the movement signal crossed the corresponding threshold level for each of the plurality of consecutive time portions of the time segment; and determining that the patient is inactive using the weighted activity levels of the time segments of the moving time window.

14. The device of claim 13, wherein generating a weighted activity level for the time segment based on the determined number of times the movement signal crossed the corresponding threshold level for each of the plurality of consecutive time portions of the time segment comprises:

defining a weight associated with each of the plurality of threshold levels;

generating a weighted activity level portion score for each of the plurality of consecutive time portions of the time segment based on the number of times that the movement signal crosses the corresponding threshold level for the consecutive time portion and the weight associated with the threshold level corresponding to the consecutive time portion; and generating the weighted activity level for each time segment of the moving time window based on the weighted activity level portion scores generated for the plurality of consecutive time portions of the time segment.

15. The device of claim 13, wherein determining a patient is inactive based on the movement signal over a moving time window comprises:

generating an activity level for the moving time window based on the generated weighted activity levels for the time segments of the moving time window; and determining that the patient is inactive based on the generated activity level for the moving time window.

16. The device of claim 15, wherein determining a patient is inactive based on the movement signal over a moving time window further comprises generating a non-weighted activity level for the moving time window, and wherein generating an activity level for the moving time window is further based on the generated non-weighted activity level for the moving time window.

17. The device of claim 11, the computing apparatus further configured to:

determine the patient is active over the moving time window; and restrict initiation of cardiac remodeling pacing in response to determining that the patient is active for a prevention time period.

18. The device of claim 17, the computing apparatus further configured to:

determine a duration of activity; and modify the prevention time period based on the duration of activity.

19. The device of claim 17, the computing apparatus further configured to execute one or more of:

modifying the prevention time period based on a time of day; and modifying the prevention time period based on a trend of patient activity.

20. The device of claim 11, the computing apparatus further configured to:

determine the patient is active over the moving time window; and terminate the cardiac remodeling pacing in response to determining that the patient is active.

21. The device of claim 11, the device further comprising one or more pacing electrodes to deliver the cardiac remodeling pacing.

22. A cardiac remodeling pacing device comprising:

one or more pacing electrodes to deliver cardiac remodeling pacing;

a movement sensor to provide a movement signal representative of movement of a patient; and a computing apparatus comprising one or more processors and operably coupled to the one or more pacing electrodes and the movement sensor, the computing apparatus configured to:

receive the movement signal from the movement sensor;

generate a weighted activity level for each time segment of a moving time window based on the movement signal;

determine that the patient is inactive using the weighted activity level for the moving time window; and deliver cardiac remodeling pacing using the one or more pacing electrodes in response to determining that the patient is inactive, wherein the cardiac remodeling pacing comprises delivery of electrical stimulation using the one or more pacing electrodes to the patient's heart to increase the patient's heart rate to lead to left ventricle wall thinning and dilation.

23. The device of claim 22, the computing apparatus further configured to:

determine the patient is active over the moving time window; and restrict initiation of cardiac remodeling pacing in response to determining that the patient is active for a prevention time period.

24. The device of claim 22, the computing apparatus further configured to:

determine the patient is active over the moving time window; and terminate the cardiac remodeling pacing in response to determining that the patient is active.

* * * * *